US005929259A

United States Patent [19]

Lockemeyer

[11] Patent Number: 5,929,259
[45] Date of Patent: *Jul. 27, 1999

[54] PREPARATION OF ETHYLENE OXIDE AND CATALYST

[75] Inventor: John Robert Lockemeyer, Sugar Land, Tex.

[73] Assignee: Shell Oil Company, Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/977,971

[22] Filed: Nov. 25, 1997

Related U.S. Application Data

[63] Continuation-in-part of application No. 08/659,479, Jun. 5, 1996, abandoned.

[51] Int. Cl.[6] ........................... C07D 301/10; B01J 23/38
[52] U.S. Cl. ........................... 549/534; 502/348; 502/351
[58] Field of Search .................................... 502/348, 351, 502/439; 549/534, 536

[56] References Cited

U.S. PATENT DOCUMENTS

| | | | |
|---|---|---|---|
| 4,141,962 | 2/1979 | Dupuy et al. | 423/571 |
| 4,621,071 | 11/1986 | Blanchard et al. | |
| 4,908,343 | 3/1990 | Bhasin | |
| 5,384,302 | 1/1995 | Gerdes et al. | 502/439 |
| 5,512,530 | 4/1996 | Gerdes et al. | 502/351 |
| 5,597,773 | 1/1997 | Evans et al. | 502/348 |

FOREIGN PATENT DOCUMENTS

96/23585  8/1996  WIPO.

*Primary Examiner*—Bekir L. Yildirim
*Attorney, Agent, or Firm*—Pamela J. McCollough

[57] ABSTRACT

This invention relates to a process for preparing an ethylene oxide catalyst by depositing silver and one or more alkali metal promoters on an alpha alumina carrier in which a fired carrier body is impregnated with a source of titania in a liquid medium that upon heating yields titania and is then calcined to generate titania uniformly dispersed in the carrier in an amount of up to about 10 percent by weight, basis the total weight of the carrier, and subsequently drying the carrier having said silver and alkali metal supported thereon.

23 Claims, No Drawings

PREPARATION OF ETHYLENE OXIDE AND CATALYST

This application is a continuation-in-part of application Ser. No. 08/659,479, filed Jun. 5, 1996, now abandoned.

FIELD OF THE INVENTION

The invention relates to a process for preparing silver-containing catalysts using carriers based on ceramic components which are suitable for the preparation of ethylene oxide and to the use of the catalysts for the preparation of ethylene oxide.

BACKGROUND OF THE INVENTION

Catalysts for the production of ethylene oxide from ethylene and molecular oxygen are generally supported silver catalysts. Such catalysts are typically promoted with alkali metals. The use of small amounts of the alkali metals potassium, rubidium and cesium were noted as useful promoters in supported silver catalysts in U.S. Pat. No. 3,962,136, issued June 8, 1976, and U.S. Pat. No. 4,010,115, issued Mar. 1, 1977. The use of other co-promoters, such as rhenium, or rhenium along with sulfur, molybdenum, tungsten and chromium is disclosed in U.S. Pat. No. 4,766,105, issued Aug. 23, 1988, and U.S. Pat. No. 4,808,738, issued Feb. 28, 1989. U.S. Pat. No. 4,908,343, issued Mar. 13, 1990, discloses a supported silver catalyst containing a mixture of a cesium salt and one or more alkali metal and alkaline earth metal salts.

The use of ceramic based catalyst carriers and specifically alpha alumina based catalyst carriers has been previously described in a number of patents such as, for example, U.S. Pat. No. 5,100,859, issued Mar. 31, 1992, U.S. Pat. No. 5,055,442, issued Oct. 8, 1991, U.S. Pat. No. 5,037,794, issued Aug. 6, 1991, and U.S. Pat. No. 4,874,739, issued Oct. 17, 1989. Such catalyst carriers have a wide variety of potential applications in the catalytic field and are especially useful where the ceramic base is an alumina such as alpha alumina.

A catalyst support needs to possess, in combination, at least a minimum surface area on which the catalytic component may be deposited, high water absorption and crush strength. The problem is that usually an increase in one can mean a reduction in another property. Thus, high crush strength may mean low porosity. Often the balance is achieved by trial and error making the catalyst carrier art even more unpredictable than other chemical process art.

Carriers based on alpha alumina have an excellent balance of crush strength, abrasion resistance, porosity and catalytic performance that makes them ideal for a range of catalytic applications. It has been found that the physical properties can be improved by incorporating a titania component into the mixture fired to produce the carrier. While such titania modification has been found to greatly improve physical properties such as crush strength and abrasion resistance, it has been found that it does tend to affect the densification of the carrier structure and this can lead to unacceptable properties. This problem increases with increasing concentration of added titania.

There is therefore a need to provide for the incorporation of the highly beneficial titania component into the carrier without causing such densification such that the catalysts prepared therefrom have acceptable physical properties and performance characteristics. The catalysts of the present invention which are prepared using these carriers have excellent physical properties and catalytic performance that make them ideal for a wide range of catalytic applications.

SUMMARY OF THE INVENTION

This invention relates to a process for preparing catalysts suitable for the production of ethylene oxide from ethylene and molecular oxygen in the vapor phase which comprises depositing a catalytically effective amount of silver and a promoting amount of alkali metal on a ceramic catalyst carrier which is prepared by a process comprising: a) forming a mixture comprising alumina components, ceramic bond, and a liquid medium; b) shaping the mixture into carrier bodies; c) drying and firing the bodies at a temperature of from about 1200° C. to about 1500° C. to form a porous carrier bodies; d) impregnating the porous carrier bodies with a titania generator in a liquid medium; and e) calcining the impregnated bodies at a temperature sufficient to remove volatiles and generate titania, and subsequently drying the carrier.

It has been found that catalysts prepared using this alpha alumina based carrier have improved initial activity and/or selectivity.

DESCRIPTION OF THE PREFERRED EMBODIMENTS

The process for preparing the catalysts of the present invention comprises depositing a catalytically effective amount of silver and a promoting amount of alkali metal on an alumina based catalyst carrier in which a fired body is impregnated with a source of titania in a liquid medium that, upon heating, yields titania, and then calcined to generate titania uniformly dispersed in the carrier in an amount of up to about 10 percent by weight. Descriptions of the carrier, the catalyst, the process for preparing the catalyst with the carrier and the use of the catalyst are provided in detail below.

The present invention provides an advance over the disclosure in U.S. Pat. No. 5,380,697, issued Jan. 10, 1995, in that it teaches the advantages of a catalyst prepared using a carrier in which addition of the titania component is by impregnation of the fired porous carrier prior to deposition of silver, alkali metal and other catalyst components on the carrier.

The Carrier

The alpha alumina based catalyst carrier of the present invention is prepared by a process which comprises:

a) forming a mixture comprising alumina components, ceramic bond, a liquid medium and optionally, organic burnout materials, shaping aids and lubricants;

b) shaping the mixture into carrier bodies;

c) drying and firing the bodies at a temperature of from about 1200° C. to about 1500° C. to form porous carrier bodies;

d) impregnating the porous carrier bodies with a titania generator in a liquid medium; and then e) calcining the impregnated bodies at a temperature sufficient to remove volatiles and generate titania.

In the discussion that follows the invention will be discussed in terms of added "titania" because, after the firing operation, it is assumed for the purposes of this specification that the titanium remaining in the carrier will be in the form of an oxide.

Since titania is not soluble in water, it must be carried in to the pores of the fired porous carrier in solution or sol form. It should be understood therefore that any suitable soluble titanium compound can be used provided that it decomposes to the oxide and leaves no residue or evolves no components that could interfere with the activity or performance of the catalyst deposited on the carrier. Thus, ammonium titanyl oxalate, titanium (IV) bis(ammonium lactato) dihydroxide, as well as any other similar organic compounds are suitable. In addition, titania sols or slurries of heat-decomposable titanium compounds are usable providing they are fluid enough to penetrate the pores of the carrier. It is also possible to use a titanium alkoxide or other organometallic compound in a suitable liquid vehicle.

As used in this specification, the term "titania generator" is understood to embrace all such suitable soluble titanium compounds, slurries and sols that, under the conditions under which the carrier is produced, form titania.

Generally, the use of a titanium salt as the titania generator is preferred and the oxalate or dihydroxy bis-lactate are the most preferred titanium salts because they are very soluble and because they decompose at relatively low temperatures of from around 200° C. to about 320° C. Upon decomposition, an amorphous titania phase is formed which generally has too high a surface area for optimum results. It is preferred to calcine the impregnated carrier at a temperature at or above about 450° C. to about 500° C. at which the anatase form is generated. Heating at higher temperatures above about 773° C. generates the rutile form. Neither of these consequences is disastrous, especially if a larger amount of titania towards the upper end of the preferred range is used, however it should be noted that prolonged exposure to higher temperatures can lead to the titania sintering and forming larger crystals which, in general, is not desirable. It is therefore desirable to calcine the impregnated carrier at a temperature in the range of from about 400° C. to about 1400° C., preferably from about 400° C. to about 700° C., and more preferably in the range of from about 500° C. to about 600° C., and for a time in the range of from about 15 minutes to about 120 minutes and preferably in the range of from about 30 minutes to about 60 minutes.

It is often found advantageous to add the titania generator in an amount which represents from about 0.05 percent to about 10 percent, and more preferably from about 0.1 percent to about 2.0 percent of the weight of the fired carrier, (calculated as $TiO_2$). Generally speaking, little selectivity advantage is seen as a result of incorporating more than about 0.5 percent of titania. Impregnation is preferably done by saturating the carrier particles with a solution of a titania generator which is then decomposed to titania when the carrier particles are calcined.

The calcination of the impregnated carrier is carried out under conditions adapted to generate titania. In the presence of alumina, the calcination can result in the formation of aluminum titanate which is, in general, less preferred than titania.

Certain forms of alumina and bond material may also contain titania as impurities or components. The contribution of such forms of titania are not included in the amounts specified above.

The carrier is heated at a temperature that is high enough to sinter the alumina particles and produce a structure with physical properties adequate to withstand the environment in which it is expected to operate. In practice, temperatures in the range of from about 1200° C. to about 1500° C. and particularly in the range of from about 1300° C. to about 1500° C. are used to perform this sintering. It should be understood that lower temperatures usually require longer times to achieve the same degree of sintering as higher temperatures. Sintering may be carried out either before or after the impregnation or if desired, at the time the catalyst components are placed on the carrier. Preferably, sintering is carried out prior to impregnation.

The preferred catalyst carrier of the invention may comprise a number of alpha alumina components chosen to contribute to the desired physical properties, including porosity, pore volume, crush strength and the like. Often, a combination of two different alpha aluminas is preferred, one component having larger particles mixed with a second component having smaller particles, in weight ratios of from about 10:90 to about 90:10. The objective of this is to end up with a surface area, (in this document a reference to "surface area" is understood to mean the BET surface area measured using nitrogen or krypton as the adsorbed gas), in the finished product of from about 0.4 square meters/gram ($m^2/g$) to about 5 $m^2/g$. The surface area in the finished carrier is somewhat less than for the free alumina particles. Thus, a convenient mixture may comprise for example, two types of alpha alumina particles, the first having a surface area of about 1 $m^2/g$ and the second having a surface area of about 3 $m^2/g$ to about 5 $m^2/g$.

Part of the alpha alumina may be formed in situ from a precursor which is preferably boehmite. Good results are also obtained if the precursor comprises a mixture of boehmite with an aluminum trihydrate such as gibbsite or bayerite. Where such a mixture is used it is often preferred to use a weight ratio of the monohydrate, (boehmite), to trihydrate of from about 1:10 to about 1:3 and more preferably from about 1:8 to about 1:4. It is often preferred that, when a sol is formed from the precursor by addition of water, a submicron particle sized seed material is also added. This has the effect of reducing the temperature at which the transition to alpha alumina occurs and reduces the crystal size of the alpha alumina produced upon transformation.

The seed used can be any material that is effective to produce nucleation sites in the precursor so as to reduce the transition temperature at which a transition alumina converts to alpha alumina. Seeds that accomplish this goal typically have the same crystal lattice type as alpha alumina itself and lattice dimensions that do not differ significantly from those of alpha alumina. Clearly, the most convenient seed is alpha alumina itself and sub-micron sized particles of alpha alumina are the preferred seed. It is, however, possible to use other seeds such as alpha ferric oxide and chromium oxide.

Alpha alumina formed from the preferred seeded precursor when the extruded mixture is fired generally has a much finer crystal size than the alpha alumina particles with which the seeded precursor is mixed unless, during firing, it is maintained at a high temperature for a prolonged period. As produced, the seeded sol-gel material has a sub-micron crystal structure but if it is held at temperatures over about 1400° C. for extended periods, crystal growth begins and the size differentiation may become less apparent.

The carrier of the invention preferably has a porosity of at least 50 percent and more desirably from about 60 percent to about 75 percent. The porosity is related to the surface area which is preferably from about 0.4 $m^2/g$ to about 5 $m^2/g$, and more preferably from about 0.6 $m^2/g$ to about 1.2 $m^2/g$. The porosity may be obtained by addition of organic burnout material such as ground walnut shells or solid particles of a combustible hydrocarbon. Porosity may also be obtained without the use of burnout material by choice of particle sizes of the ceramic components sintered together to form the carrier.

It is usually preferred to add a ceramic bond material to the mixture from which the carrier is to be made to give added strength to the fired carrier. Conventional ceramic bond materials can be used and after firing these typically comprise components, (expressed as the oxides), such as silica, alumina, alkaline earth metal oxides, alkali metal oxides, iron oxide and titanium oxide, with the first two being the dominant components. It is found that bond materials containing significant amounts of alki metals, that is up to about 5 percent by weight and more preferably from about 2 percent by weight to 4 percent by weight are particularly suitable. Particularly suitable bond materials include calcium silicate and magnesium silicate either added as such or formed in situ.

The carriers described above are particularly suited for preparing ethylene oxide catalysts which have improved physical properties with respect to crush strength and abrasion resistance.

The Catalyst

The catalysts of the present invention are prepared by depositing a catalytically effective amount of silver and a promoting amount of alkali metal(s) on a carrier prepared by a process which comprises: a) forming a mixture comprising alumina components, ceramic bond, a liquid medium and optionally, organic burnout materials, shaping aids and lubricants; b) shaping the mixture into carrier bodies; c) drying and firing the bodies at a temperature of from about 1200° C. to about 1500° C. to form a porous carrier bodies; d) impregnating the porous carrier bodies with a titania generator in a liquid medium; and then e) firing the impregnated bodies at a temperature sufficient to remove volatiles and generate titania, and subsequently drying the carrier having said silver and alkali metal(s) deposited thereon. Other catalyst promoters in promoting amounts may be optionally present such as rare earths, magnesium, rhenium and rhenium copromoters selected from sulfur, chromium, molybdenum, tungsten, phosphorus, boron and mixtures thereof.

In general, the catalysts of the present invention are prepared by impregnating porous refractory supports comprising alpha alumina with silver ions or compound(s), complex(es) and/or salt(s) dissolved in a suitable solvent sufficient to cause deposition on the support of from about 1 to about 40, preferably from about 1 to about 30 percent by weight, basis the weight of the total catalyst, of silver. The impregnated support is then separated from the solution and the deposited silver compound is reduced to metallic silver. Also deposited on the support either prior to, coincidentally with, or subsequent to the deposition of the silver will be suitable ions, or compound(s) and/or salt(s) of alkali metal dissolved in a suitable solvent. Also deposited on the carrier coincidentally with the deposition of the silver and/or alkali metal will be suitable optional promoter compound(s), complex(es) and/or salt(s) dissolved in an appropriate solvent.

The catalysts of the present invention are prepared by a technique in which the alkali metal promoter as well as any additional promoters in the form of soluble salts and/or compounds are deposited on the catalyst and/or support prior to, simultaneously with, or subsequent to the deposition of the silver and each other. The preferred method is to deposit silver, alkali metal and any additional promoters simultaneously on the support, that is, in a single impregnation step, although it is believed that the individual or concurrent deposition of the alki metal prior to and/or subsequent to the deposition of the silver would also produce suitable catalysts.

Promoting amounts of alkali metal or mixtures of alkali metal are deposited on a porous support using a suitable solution. Although alkali metals exist in a pure metallic state, they are not suitable for use in that form. They are used as ions or compounds of alkali metals dissolved in a suitable solvent for impregnation purposes. The carrier is impregnated with a solution of alkali metal promoter ions, salt(s) and/or compound(s) before, during or after impregnation of the silver ions or salt(s), complex(es), and/or compound(s) has taken place. An alkali metal promoter may even be deposited on the carrier after reduction to metallic silver has taken place. The promoting amount of alkali metal utilized will depend on several variables, such as, for example, the surface area and pore structure and surface chemical properties of the carrier used, the silver content of the catalyst and the particular ions used in conjunction with the alkali metal cation, optional co-promoters. The amount of alkali metal promoter deposited upon the support or present on the catalyst generally lies between about 10 parts per million and about 3000 parts per million, preferably between about 15 parts per million and about 2000 parts per million and more preferably, between about 20 parts per million and about 1500 parts per million by weight of total catalyst. Most preferably, the amount ranges between about 50 parts per million and about 1000 parts per million by weight of the total catalyst. The degree of benefit obtained within the above-defined limits will vary depending upon particular properties and characteristics, such as, for example, reaction conditions, catalyst preparative techniques, surface area and pore structure and surface chemical properties of the carrier utilized, silver content of the catalyst, and other compounds, cations or anions present in addition to alkali metal ions, and the above-defined limits were selected to cover the widest possible variations in properties and characteristics. The effects of these variation in properties are readily determined by experimentation. The alkali metal promoters are present on the catalysts in the form of cations (ions) or compounds of complexes or surface compounds or surface complexes rather than as the extremely active free alkali metals, although for convenience purposes in this specification and claims they are referred to as "alkali metal" or "alkali metal promoters" even though they are not present on the catalyst as metallic elements. For purposes of convenience, the amount of alkali metal deposited on the support or present on the catalyst is expressed as the metal. Without intending to limit the scope of the invention, it is believed that the alkali metal compounds are oxidic compounds. More particularly, it is believed that the alkali metal compounds are probably in the form of mixed surface oxides or double surface oxides or complex surface oxides with the aluminum of the support and/or the silver of the catalyst, possibly in combination with species contained in or formed from the reaction mixture, such as, for example, chlorides or carbonates or residual species from the impregnating solution(s).

In a preferred embodiment, at least a major proportion (greater than 50% wt.) of the alkali metals are selected from the group consisting of potassium, rubidium, cesium, and mixtures thereof. As used herein, the term "alkali metal" and cognates thereof refers, to the alkali metals selected from the group consisting of lithium, sodium, potassium, rubidium, cesium and mixtures thereof. As used herein, the term "mixtures of alkali metals" or cognates of these terms refers to the use of two or more of the alkali metals, as appropriate, to provide a promoting effect. Non-limiting examples include cesium plus rubidium, cesium plus potassium, cesium plus sodium, cesium plus lithium, cesium plus rubidium plus sodium, cesium plus potassium plus sodium, cesium plus lithium plus sodium, cesium plus rubidium plus potassium plus sodium, cesium plus rubidium plus potassium plus lithium, cesium plus potassium plus lithium and the like. A preferred alkali metal promoter is cesium.

It should be understood that the amounts of alkali metal promoters on the catalysts are not necessarily the total amounts of these metals present in the catalyst. Rather, they are the amounts of alkali metal promoters which have been added to the catalyst by impregnation with a suitable solution of ions, salts and/or compounds and/or complexes of alkali metals. These amounts do not include amounts of alkali metals which are locked into the support, for example, by calcining, or are not extractable in a suitable solvent such as water or lower alkanol or amine or mixtures thereof and do not provide a promoting effect. It is also understood that a source of the alkali metal promoter ions, salts and/or compounds used to promote the catalyst may be the carrier. That is, the carrier may contain extractable amounts of alkali metal that can be extracted with a suitable solvent, such as water or lower alkanol. Thus, a catalyst prepared using such a carrier and an impregnating solution containing water or lower alkanol will have the alkali metal ions, salts and/or compounds deposited or redeposited on the catalyst.

Non-limiting examples of other promoters include rhenium, sulfate, molybdate, tungstate and chromate (see U.S. Pat. No. 4,766,105, issued Aug. 23, 1988), as well as phosphate and borate; sulfate anion, fluoride anion, oxyanions of Groups 3b to 6b (see U.S. Pat. No. 5,102,848, issued Apr. 7, 1992); (i) oxyanions of an element selected from Groups 3 through 7b and (ii) alkali(ne) metal salts with anions of halides, and oxyanions selected from Groups 3a to 7a and 3b through 7b (see U.S. Pat. No. 4,908,343, issued Mar. 13, 1990).

As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "Manion" being negative. The term "oxyanionic" or "oxyanion" refers to a negatively charged moiety containing at least one oxygen atom in combination with another element. An oxyanion is thus an oxygen-containing anion. It is understood that ions do not exist as independent or discrete entities, but are found in combination with charge-balancing counterions. The term "oxidic" refers to a charged or neutral species wherein an element in question is bound to oxygen and possibly one or more different elements by surface and/or chemical bonding, such as ionic and/or covalent and/or coordinate bonding. Thus, an oxidic compound is an oxygencontaining compound which also may be a mixed, double or complex surface oxide. Illustrative oxidic compounds include, by way of non-limiting examples, oxides (containing only oxygen as the second element), hydroxides, nitrates, sulfates, carboxylates, carbonates, bicarbonates, oxyhalides, etc. as well as surface species wherein the element in question is bound directly or indirectly to an oxygen either in the substrate or the surface.

As used herein, the term "promoting amount" of a certain component of a catalyst refers to an amount of that component which works effectively to provide an improvement in one or more of the catalytic properties of that catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced and may even be diminished. It is further understood that different catalytic properties may be enhanced at different operation conditions. For example, a catalyst having enhanced selectivity at one set of operating conditions may be operated at a different set of conditions wherein the improvement shows up in the activity rather that the selectivity and an operator of an ethylene oxide plant will intentionally change the operation conditions in order to take advantage of certain catalytic properties even at the expense of other catalytic properties in order to maximize profits by taking into account feedstock costs, energy costs, by-product removal costs and the like.

As used herein, the term "catalytically effective amount of silver" refers to an amount of silver that provides a measurable conversion of ethylene and oxygen to ethylene oxide.

Generally, the carrier is contacted with a silver salt, a silver compound, or a silver complex which has been dissolved in an aqueous solution, so that the carrier is impregnated with said aqueous solution; thereafter the impregnated carrier is separated from the aqueous solution, e.g., by centrifugation or filtration and then dried. The thus obtained impregnated carrier is heated to reduce the silver to metallic silver. It is conveniently heated to a temperature in the range of from about 50° C. to about 300° C., during a period sufficient to cause reduction of the silver salt, compound or complex to metallic silver and to form a layer of finely divided silver, which is bound to the surface of the carrier, both the exterior and pore surface. Air, or other oxidizing gas, reducing gas, an inert gas or mixtures thereof may be conducted over the carrier during this heating step.

There are several known methods to add the silver to the carrier or support. The carrier may be impregnated with an aqueous solution containing silver nitrate dissolved therein, and then dried, after which drying step the silver nitrate is reduced with hydrogen or hydrazine. The carrier may also be impregnated with an ammoniacal solution of silver oxalate or silver carbonate, and then dried, after which drying step the silver oxalate or silver carbonate is reduced to metallic silver by heating, e.g., to about 600° C. Specific solutions of silver salts with solubilizing and reducing agents may be employed as well, e.g., combinations of the vicinal alkanolamines, alkyldiamines and ammonia. One such example of a solution of silver salts comprises an impregnating solution comprising a silver salt of a carboxylic acid, an organic amine solubilizing/reducing agent, and an aqueous solvent.

Suitable silver salts include silver carbonate and the silver salts of mono- and polybasic carboxylic and hydroxycarboxylic acids of up to about 16 carbon atoms. Silver carbonate and silver oxalate are particularly useful silver salts, with silver oxalate being most preferred.

An organic amine solubilizing/reducing agent is present in the impregnating solution. Suitable organic amine silver-solubilizing/reducing agents include lower alkylenediamines of from 1 to 5 carbon atoms, mixtures of a lower alkanolamine of from 1 to 5 carbon atoms with a lower alkylenediamine of from 1 to 5 carbon atoms, as well as mixtures of ammonia with lower alkanolamines or lower alkylenediamines of from 1 to 5 carbons. Four groups of organic amine solubilizing/reducing agents are particularly useful. The four groups include vicinal alkylenediamines of from 2 to 4 carbon atoms, mixtures of (1) vicinal alkanolamines of from 2 to 4 carbon atoms and (2) vicinal alkylenediamines of from 2 to 4 carbon atoms, mixtures of vicinal alkylenediamines of from 2 to 4 carbon atoms and ammonia, and mixtures of vicinal alkanolamines of from 2 to 4 carbon atoms and ammonia. These solubilizing/reducing agents are generally added in the amount of from about 0.1 to about 10 moles per mole of silver present.

Particularly preferred solubilizing/reducing agents are ethylenediamine, ethylenediamine in combination with ethanolamine, ethylenediamine in combination with ammonia, and ethanolamine in combination with ammonia, with ethylenediamine being most preferred. Ethylenediamine in combination with ethanolamine gives comparable results.

When ethylenediamine is used as the sole solubilizing/reducing agent, it is necessary to add amounts of the amine in the range of from about 0.1 to about 5.0 moles of ethylenediamine per mole of silver.

When ethylenediamine and ethanolamine together are used as the solubilizing/reducing agent, it is suitable to employ from about 0.1 to about 3.0 moles of ethylenediamine per mole of silver and from about 0.1 to about 2.0 moles of ethanolamine per mole of silver.

When ethylenediamine or ethanolamine is used with ammonia, it is generally useful to add at least about two moles of ammonia per mole of silver and very suitable to add from about 2 to about 10 moles of ammonia per mole of silver. The amount of ethylenediamine or ethanolamine employed then is suitably from 0.1 to 2.0 moles per mole of silver.

One method of preparing the silver containing catalyst can be found in U.S. Pat. No. 3,702,259, issued Nov. 7, 1972, incorporated by reference herein. Other methods for preparing the silvercontaining catalysts which in addition contain higher alkali metal promoters can be found in U.S. Pat. No. 4,010,115, issued Mar. 1, 1977; and U.S. Pat. No. 4,356,312, issued Oct. 26, 1982; U.S. Pat. No. 3,962,136, issued Jun. 8, 1976 and U.S. Pat. No. 4,012,425, issued Mar. 15, 1977, all incorporated by reference herein. Methods for preparing silver-containing catalysts containing higher alkali metal and rhenium promoters can be found in U.S. Pat. No. 4,761,394, issued Aug. 2, 1988, which is incorporated by reference herein, and methods for silver-containing catalysts containing higher alkali metal and rhenium promoters and a rhenium co-promoters can be found in U.S. Pat. No. 4,766,105, issued Aug. 2, 1988, which is incorporated herein by reference. Methods for preparing silver-containing catalysts with a variety of different promoters are found in U.S. Pat. Nos. 4,908,343, issued Mar. 13, 1990 and 5,057,481, issued Oct. 15, 1991, both incorporated herein by reference.

A particularly preferred process of impregnating the carrier consists of impregnating the carrier with an aqueous solution containing a silver salt of a carboxylic acid, an organic amine and a salt of cesium and a salt of an additional alkali dissolved therein. Silver oxalate is a preferred salt. It can be prepared by reacting silver oxide (slurry in water) with (a) a mixture of ethylenediamine and oxalic acid, or (b) oxalic acid and then ethylenediamine, which latter is preferred, so that an aqueous solution of silver oxalate-ethylenediamine complex is obtained, to which solution is added a certain amount of cesium compound and a certain amount of an additional alkali metal compound. Other diamines and other amines, such as ethanolamine, may be added as well. A cesium-containing silver oxalate solution may also be prepared by precipitating silver oxalate from a solution of cesium oxalate and silver nitrate and rinsing with water or alcohol the obtained silver oxalate in order to remove the adhering cesium salt until the desired cesium content is obtained. The cesium-containing silver oxalate is then solubilized with ammonia and/or an amine in water. Rubidium-, potassium-, sodium-, lithium- and mixtures of alkali metal-containing solutions may be prepared also in these ways. The impregnated carriers are then heated to a temperature between about 50° C. and about 600° C., preferably between about 75° C. and about 400° C. to evaporate the liquid and produce a metallic silver.

In general terms, the impregnation process comprises impregnating the support with one or more solutions comprising silver, alkali metal and optionally, other promoters. As used in the instant specification and claims, the terminology "impregnating the support with one or more solutions comprising silver, alkali metal, and optional other promoters" and similar or cognate terminology means that the support is impregnated in a single or multiple impregnation with one solution containing silver, alkali metal, and optional other promoters in differing amounts; or in multiple impregnations with two or more solutions, wherein each solution contains at least one component selected from silver, alkali metal, and optional other promoter(s), with the proviso that all of the components of silver and alkali metal will individually be found in at least one of the solutions. The concentration of the silver (expressed as the metal) in the silver-containing solution will range from about 1 g/l up to the solubility limit when a single impregnation is utilized. The concentration of the alkali metal (expressed as the metal) will range from about $1 \times 10^{-3}$ g/l up to about 12 g/l and preferably, from about $10 \times 10^{-3}$ g/l to about 12 g/l when a single impregnation step is utilized. Concentrations selected within the above noted ranges will depend upon the pore volume of the catalyst, the final amount desired in the final catalyst and whether the impregnation is single or multiple. Appropriate concentrations can be readily determined by routine experimentation.

It is observed that independent of the form in which the silver is present in the solution before precipitation on the carrier, the term "reduction to metallic silver" is used, while in the meantime often decomposition by heating occurs. We prefer to use the term "reduction", since $Ag^+$ ion is converted into a metallic Ag atom. Reduction times may generally vary from about 0.5 minute to about 8 hours, depending on the circumstances.

The Process

In commercial operation, ethylene and oxygen are converted to ethylene oxide in an ethylene oxide reactor which comprises a large fixed tube heat exchanger containing several thousand tubes filled with catalysts. A coolant is used on the shell side of the reactor to remove the heat of reaction. Coolant temperatures are frequently utilized as an indication of catalyst activity, with high coolant temperatures corresponding to lower catalyst activities.

In the reaction of ethylene oxide with oxygen to produce ethylene oxide, the ethylene is typically present in at least a double amount (on a molar basis) compared with oxygen, but the amount of ethylene employed is generally much higher. The conversion is therefore conveniently calculated according to the mole percentage of oxygen which has been consumed in the reaction to form ethylene oxide and any oxygenated by-products. The oxygen conversion is dependent on the reaction temperature, and the reaction temperature is a measure of the activity of the catalyst employed. The value $T_{1.5}$ indicates the temperature at 1.5 percent ethylene oxide production, and the value T is expressed in ° C. This temperature for any given catalyst is higher when the conversion of oxygen is higher. Moreover, this temperature is strongly dependent on the employed catalyst and the reaction conditions. The selectivity (to ethylene oxide) indicates the molar amount of ethylene oxide in the reaction product compared with the total molar amount of ethylene converted. In this specification, the selectivity is indicated as $S_{1.5}$, which means the selectivity at 1.5 percent ethylene oxide production.

The conditions for carrying out such an oxidation reaction in the presence of the silver catalysts according to the present invention broadly comprise those already described in the prior art. This applies, for example, to suitable temperatures, pressures, residence times, diluent materials such as nitrogen, carbon dioxide, steam, argon, methane or other saturated hydrocarbons, to the presence of moderating agents to control the catalytic action, for example, 1–2-dichloroethane, vinyl chloride, ethyl chloride or chlorinated polyphenyl compounds, to the desirability of employing recycle operations or applying successive conversions in different reactors to increase the yields of ethylene oxide, and to any other special conditions which may be selected in processes for preparing ethylene oxide. Pressures in the range of from atmospheric to about 500 psig are generally employed. Higher pressures, however, are not excluded. Molecular oxygen employed as reactant can be obtained from conventional sources. The suitable oxygen charge may consist essentially or relatively pure oxygen, a concentrated oxygen stream comprising oxygen in major amount with lesser amounts of one or more diluents, such as nitrogen and argon, or another oxygen-containing stream, such as air. It is therefore evident that the use of the present silver catalysts in ethylene oxide reactions is in no way limited to the use of specific conditions among those which are known to be effective. For purposes of illustration only, the following table shows the range of conditions that are often used in current commercial ethylene oxide reactor units and which are also suitable for the instant process.

TABLE I

| *GHSV | 1500–10,000 |
|---|---|
| Inlet Pressure | 150–400 psig |
| Inlet Feed | |
| Ethylene | 1–40% |
| $O_2$ | 3–12% |
| Ethane | 0–3% |
| Chlorohydrocarbon moderator | 0.3–50 ppmv total |
| Argon and/or methane and/or nitrogen diluent | Balance |
| Coolant temperature | 180–315° C. |
| Catalyst temperature | 180–325° C. |
| $O_2$ conversion level | 10–60% |
| EO Production (Work Rate) | 2–25 lbs. EO/cu. ft. catalyst/hr. |

*Cubic feet of gas at standard temperature and pressure passing over one cubic foot of packed catalyst per hour.

In a preferred application of the silver catalysts according to the invention, ethylene oxide is produced when an oxygen-containing gas is contacted with ethylene in the presence of the present catalysts at a temperature in the range of from about 180° C. to about 330° C., and preferably a temperature in the range of from about 200° C. to about 325° C.

While the catalysts of the present invention are preferably used to convert ethylene and oxygen to ethylene oxide, olefins having three or more carbon atoms can be oxidized using the silver catalysts of the present invention to produce a high selectivity of epoxide derivatives thereof by contacting the olefin feed with an oxygen-containing gas in the presence of an organic halide and the silver catalyst described above under defined oxidation conditions. The catalysts of the present invention may also be utilize to oxidize mixtures of olefins.

The process for the selective epoxidation of olefins having at least three carbon atoms comprises contacting the feed olefin with a sufficient quantity of an oxygen-containing gas so as to maintain the molar ratio of olefin to oxygen in the range of about 0.01 up to about 20, in the presence of an organic halide and a silver catalyst at a reaction pressure in the range of about 0.1 up to about 100 atmospheres and a temperature in the range of about 75° up to about 325° C. for a reaction time sufficient to obtain olefin conversions per pass in the range of about 0.1 up to about 75 mole percent.

Olefins contemplated for use in this oxidation process are those which satisfy the following structural formula:

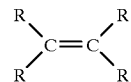

wherein each R is independently selected from the group consisting of:
(a) hydrogen,
(b) aryl and substituted aryl groups having in the range of 6 up to 20 carbon atoms,
(c) alkyl groups of the formula:

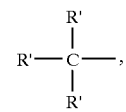

where each R' is independently:

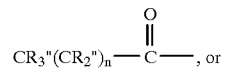

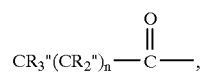

where R" is H, $C_1$–$C_{10}$ alkyl or substituted alkyl, an aryl or substituted aryl group having 6 up to 20 carbon atoms, and n is a whole number from 0–12;
(d) $CR_3''$—$(CR_2'')_x$—O—, where x is a whole number from 1–12;

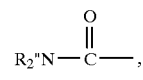

(f) $R_2''N$—;
(g) $R''S$—;

(h) $CR_2''=CR''$—$(CR''=CR'')_y$—, where y is an integer from 0–20; and

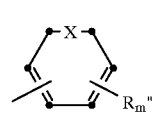

(i)

where X is O, S or NR"; and m is an integer from 0–3 with the proviso that at least one R-group not be hydrogen.

Exemplary olefins which satisfy the above structural formula include butadiene, tertary butylethylene, vinyl furan, methyl vinyl ketone, N-vinyl pyrrolidone, and the like. A presently preferred olefin for use in the practice of this process is butadiene because of its ready availability, relatively low cost, and the wide range of possible uses for the epoxide reaction product.

The epoxides produced by this process have the structural formula:

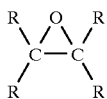

wherein each R is independently defined as set forth above. Where one or more of the R-groups contain carbon-carbon bond unsaturation, further oxidation can be carried out, thereby producing polyepoxide products.

The process is carried out by contacting the olefin to be oxidized with molecular oxygen and an organic halide under oxidation conditions, i.e. in the presence of sufficient quantities of an oxygen-containing gas to provide a molar ratio of olefin to oxygen in the range of about 0.01 up to about 20, and in the presence of about 0.1 up to about 1000 parts per million (by volume of total feed) of organic halide. Preferred quantities of organic halide for use in the practice of the present invention fall within the range of about 1 up to about 100 parts per million, by volume of total feed.

While greater or lesser quantities of molecular oxygen can be employed, sufficient quantities of oxygen should be provided to insure that undesirably low levels of olefin conversion do not occur, while excessively high oxygen concentrations should be avoided to prevent the formation of explosive mixtures. Similarly, lower levels of organic halide will provide negligible effect on catalyst performance, while higher levels of organic halide would not be expected to provide any significant improvement in catalyst performance.

Suitable oxygen-containing gases include air, oxygen enriched air, substantially purified oxygen, oxygen diluted with inert gases such as $N_2$, Ar, $CO_2$, $CH_4$ and the like.

The organic halide can be added to the oxidation reaction zone in a variety of ways. For example, it can be mixed with the olefin to be oxidized and/or the oxygen-containing gas prior to contacting with the catalyst, or the organic halide can be introduced to the reaction zone separately from the feed olefin and/or the oxygen-containing gas.

Suitable reaction temperatures fall within the range of about 75° C. up to about 325° C. At lower temperatures, the reaction proceeds so slowly as to be impractical, while at higher temperatures undesirable levels of by-products, e.g. carbon dioxide, are obtained. Preferred reaction temperatures fall within the range of about 125° C. up to about 295° C.; with temperatures in the range of about 175° C. up to about 290° C. being most preferred because selectivity to the desired epoxide falls off at temperatures significantly above about 290° C. and space-time yields are undesirably low at temperatures below about 175° C.

The reaction pressure can vary within wide ranges, with typical limits of about 0.1 up to about 100 atmospheres being chosen primarily as a function of safety, handling, equipment, and other practical considerations. Preferably, reaction pressure is maintained in the range of about 1 up to about 30 atmospheres.

Reaction times suitable for this process can vary within wide ranges. Generally, olefin, oxygen, organic halide and catalyst are maintained in contact for a time sufficient to obtain olefin conversions per pass in the range of about 0.1 up to about 75 mole percent. Preferred target olefin conversion levels per pass fall within the range of about 1 up to about 50 mole percent, while reaction times sufficient to obtain olefin conversion per pass in the range of about 5 up to about 30 mole percent are presently most preferred for efficient utilization of the reactor capacity.

Those of skill in the art recognize that the actual contact times required to accomplish the desired conversion levels can vary within wide ranges, depending on such factors as vessel size, olefin to oxygen ratios, the silver loading level on the catalyst, the presence or absence of any catalyst modifiers (and their loading levels), the amount of organic halide present in the reaction zone, the reaction temperature and pressure, and the like.

The process can be carried out in either batch or continuous mode. Continuous reaction is presently preferred since high reactor throughput and high purity product is obtained in this manner. The batch mode is satisfactorily employed when high volume of reactant throughput is not required, for example, for liquid phase reactions.

For continuous mode of reaction carried out in the gas phase, typical gas hourly space velocities (GHSV) fall within the range of about 100 up to 30,000 $hr^{-1}$. GHSV in the range of about 200 up to 20,000 $hr^{-1}$ are preferred, with GHSV in the range of about 300 up to 10,000 $hr^{-1}$ being most preferred because under such conditions the most desirable combination of feed olefin conversion and product selectivities are obtained.

When continuous mode of reaction is carried out in the liquid phase, typical liquid hourly space velocities (LHSV) employed will give contact times analogous to that obtained at the GHSV values given above. Most preferably, LHSV employed win fall in the range so as to produce the most desirable combination of feed olefin conversion levels and high product selectivity.

Recovery of the epoxide product produced can readily be carried out employing techniques well known by those of skill in the art. For example, where reaction is carried out in the continuous mode, unreacted starting material is initially separated from reaction products; and the desired product then isolated from the resulting product mixture by distillation, crystallization, extraction, or the like. Since the selectivity to the desired epoxide product is generally quite high, there are only small amounts of undesired reaction products from which to isolate the desired product.

Prior to use for oxidizing olefins having at least three carbon atoms, the silver catalysts (either before or after further treatment with promoter), are optionally calcined in an oxygen-containing atmosphere (air or oxygen-supplemented helium) at about 350° C. for about 4 hours. Following calcination, the silver catalysts are typically subjected to an activation treatment at a temperature in the range of about 300°–350° C. in an atmosphere initially containing about 2–5% hydrogen in an inert carrier such as helium or nitrogen. The hydrogen content of the activating atmosphere is gradually increased up to a final hydrogen concentration of about 20–25% at a controlled rate so that the activation temperature does not exceed 350° C. After the temperature is maintained for about 1 hour at a hydrogen concentration in the range of about 20–25 %, catalyst is ready for use.

More detailed descriptions of the silver catalysts and their use in oxidizing olefins having at least three carbon atoms are found in U.S. Pat. Nos. 4,897,498, issued Jan. 30, 1990 and 5,081,096, issued Jan. 14, 1992, both of which are incorporated by reference herein.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The invention will be illustrated by the following illustrative embodiments which are provided for illustration only and are not intended to limit the scope of the instant invention.

ILLUSTRATIVE EMBODIMENTS

Carrier Preparation

Carrier A:

The ceramic components are mixed with a burn-out material (walnut shell flour), and boric acid for about a minute. Water and an alpha alumina seed component are then added, the water being added in an amount that is necessary to make the mixture extrudable. Generally this is about 30% by weight of the total solids present. The mixture is mixed for about 4.5 minutes and then about 5% by weight based on the weight of the ceramic components, of vaseline is added as an extrusion aid. The mixture is then mixed for a further 3.5 minutes before being extruded in the form of hollow cylinders and dried to remove essentially all bound water. These were then fired in a tunnel kiln with a maximum temperature of about 1460–1490° C. for about 5 hours.

The fired carrier was divided into two portions and one portion was impregnated with a titania-generating material in an amount sufficient to give a final titanium content in the dried and finished carrier of 0.05 percent by weight.

The impregnation was carried out by weighing out a solution of titanium(IV) bis(ammonium lactato) dihydroxide, commercially available as "TYZOR LA", in an amount necessary to give a final level titanium content in the final carrier of 0.05 percent by weight. The total volume of solution used was equivalent to the pore volume of the carrier.

The carrier was impregnated by slow addition to the carrier in pellet form with agitation. When addition was complete, the impregnated carrier was allowed to stand for thirty minutes and then dried overnight at 120° C. It was then calcined at 500° C. for six hours. The carrier is described in terms of its formulation in Table 1 and in terms of its physical properties in Table 2.

Carrier B:

Carrier B was prepared in a manner similar to Carrier A except that the impregnation was done with deionized water containing no titania-generating material. The carrier is described in terms of its formulation in Table 1 and in terms of its physical properties in Table 2.

Carrier C:

Carrier C was prepared in a manner similar to Carrier A except that the carrier contains no alpha alumina component generated by a sol-gel process, and no seed component, i.e., Alpha Alumina #5, was added to the carrier formulation. The carrier is described in terms of its formulation in Table 1 and in terms of its physical properties in Table 2.

Carrier D:

Carrier D was prepared in a manner similar to Carrier C except that the impregnation was done with deionized water containing no titania-generating material. The carrier is described in terms of its formulation in Table 1 and in terms of its physical properties in Table 2.

TABLE 1

CARRIER COMPOSITIONS

| | Carrier A, % wt. | Carrier B, % wt. | Carrier C, % wt. | Carrier D, % wt. |
|---|---|---|---|---|
| Alpha Alumina #1[1,2] | 46.7 | 46.7 | None | None |
| Alpha Alumina #2[1,3] | 27.4 | 27.4 | None | None |
| Alpha Alumina #3 (Seed)[1,4] | 2.2 | 2.2 | None | None |
| Alpha Alumina #4[1,5] | None | None | 74.5 | 74.5 |
| Alpha Alumina #5[1,6] | None | None | 24.5 | 24.5 |
| Titanium[1] | 0.05 | None | 0.05 | None |
| Gibbsite[1,7] | 18.3 | 18.7 | None | None |
| Boehmite[1,8] | 4.1 | 4.5 | None | None |
| Ceramic Bond[1,9,10] | 1.3 | 1.3 | 1.0 | 1.0 |
| Organic Burnout[11] | 20.0 | 11.0 | 25.0 | 25.0 |
| Vaseline[11] | 5.0 | 5.0 | 5.0 | 5.0 |
| Boric Acid[11] | 0.15 | 0.15 | 0.1 | 0.1 |
| Water (to make extrudable)[12] | ~30 | ~30 | ~30 | ~30 |

[1]Indicates "ceramic components" and percentages given are based on 100% of the ceramic components.
[2]"Alpha Alumina #1" is an alpha alumina that had a median particle size of about 3 to about 3.4 microns, a BET surface area of about 0.9 to about 1.4 m²/g, a crystallite size of about 1.6 to about 2.2 microns and a soda content of about 0.02% to about 0.06%.
[3]"Alpha Alumina #2" is an alpha alumina with a median particle size of about 4.0 to about 8.0 microns, a surface area of about 3.0 to about 5.0 m²/g, a crystallite size of from about 0.4 to about 0.8 micron and a soda content of about 0.1% to about 0.3%.
[4]"Alpha Alumina #3" is an alpha alumina that was used as the seed for the gibbsite and boehmite precursors of alpha alumina. Its median particle size was less than 0.1 micron.
[5]"Alpha Alumina #4" is an alpha alumina that had a median particle size of about 3.0 to about 4.0 microns, a crystallite size of about 3.0 to about 3.2 microns and a soda content of about 0.02% to about 0.03%.
[6]"Alpha Alumina #5" is an alpha alumina with a median particle size of about 2.5 to about 3.7 microns, a crystallite size of from about 2.0 to about 2.5 microns and a soda content of about 0.08% to about 0.10%.
[7]The gibbsite had a median particle size of from about 4.0 to about 20 microns.
[8]The boehmite was dispersible as a sol.
[9]The ceramic bond for carriers A and B contained components, expressed as the oxides, in the following approximate proportions: 61.3% wt. SiO$_2$, 28.6% wt. Al$_2$O$_3$, 0.85% wt. Fe$_2$O$_3$, 0.68% wt. TiO$_2$, 2.92% wt. CaO, 1.79% wt. MgO, 1.15% wt. Na$_2$O and 2.67% wt. K$_2$O.
[10]The ceramic bond for carriers C and D contained components, expressed as the oxides, in the following approximate proportions: 58.76% wt. SiO$_2$, 36.55% wt. Al$_2$O$_3$, 1.22% wt. Fe$_2$O$_3$, 1.51% wt. TiO$_2$, 0.90% wt. CaO, 0.26% wt. MgO, 0.11% wt. Na$_2$O, and 0.57% wt. K$_2$O.
[11]Percentages are based on the total weight of the ceramic components.
[12]Percentages are based on total weight of solids.

TABLE 2

CARRIER PROPERTIES

| PROPERTY | Carrier A | Carrier B | Carrier C | Carrier D |
|---|---|---|---|---|
| Fired Temp. ° C. | 500 | 500 | 500 | 500 |
| Surface Area[1] (m²/g) | 1.06 | 1.06 | 0.5 | 0.5 |
| Pack. Den.[2] (lb/ft³) | 44.6 | 44.6 | 46.1 | 46.1 |
| Water Absorp.[3] (%) | 45.9 | 45.9 | 43.9 | 43.9 |

[1]"Surface Area" is the BET surface area measured using nitrogen or krypton as the adsorbate.
[2]"Packing Density" is the settled packing density as measured by ASTM D-4699-87, modified by the use of cylinder with an inside diameter of 3¾ inches and a length of 18 inches, or an equivalent.
[3]"Water Absorption" is a measure of the increase in weight of the carrier after being immersed in water and weighed.

Catalyst Preparation

The following illustrative embodiment describes preparative techniques for making the catalysts of the instant invention (Catalysts A and C) and the comparative catalysts (Comparative Catalysts B and D) and the technique for measuring the properties of these catalysts.

Part A: Preparation of stock silver oxalate/ethylene-diamine solution for use in catalyst preparation:

1) Dissolve 415 grams (g) of reagent-grade sodium hydroxide in 2340 milliters (ml) deionized water. Adjust the temperature to 50° C.

2) Dissolve 1699 g of (high purity) silver nitrate in 2100 ml deionized water. Adjust the temperature to 50° C.

3) Add sodium hydroxide solution slowly to silver nitrate solution with stiring while maintaining a temperature of 50° C. Stir for 15 minutes after addition is complete, and then lower the temperature to 40° C.

4) Insert clean filter wands and withdraw as much water as possible from the precipitate created in step (3) in order to remove sodium and nitrate ions. Measure the conductivity of the water removed and add back as much fresh deionized water as was removed by the filter wands. Stir for 15 minutes at 40° C. Repeat this process until the conductivity of the water removed is less than 90 $\mu$mho/cm. Then add back 1500 ml deionized water.

5) Add 630 g of high-purity oxalic acid dihydrate in approximately 100 g increments. Keep the temperature at 40° C. and stir to mix thoroughly. Add the last portion of oxalic acid dihydrate slowly and monitor pH to ensure that pH does not drop below 7.8.

6) Remove as much water from the mixture as possible using clean filter wands in order to form a highly concentrated silver-containing slurry. Cool the silver oxalate slurry to 30° C.

7) Add 699 g of 92 percent weight (% w) ethylenediamine (8% deionized water). Do not allow the temperature to exceed 30° C. during addition.

The above procedure yields a solution containing approximately 27–33 % w silver which provides the stock solution used in the preparation of Catalysts A and C and Comparative Catalysts B and D below.

Part B: Preparation of impregnation solutions
For Catalyst A:

To 201 grams of silver stock solution with a specific gravity of 1.562 was added 0.0386 grams of $NH_4F$ in 2 cc of water. CsOH (50% solution in water) in an amount of 0.1346 grams was added to 50 grams of the above silver solution and the resulting mixture was used for the carrier impregnation.

For Comparative Catalyst B:

To 153 grams of silver stock solution with a specific gravity of 1.443 was added 0.0290 grams of $NH_4F$ in 2 cc of water. CsOH (50% solution in water) in an amount of 0.1101 grams was added to 50 grams of the above silver solution and the resulting mixture was used for the carrier impregnation.

For Catalyst C:

To 108 grams of silver stock solution with a specific gravity of 1.542 was diluted with 10.7 grams of water. CsOH (50% solution in water) in an amount of 0.0422 grams was added to 36 grams of the above silver solution and the resulting mixture was used for the carrier impregnation.

For Comparative Catalyst D:

To 108 grams of silver stock solution with a specific gravity of 1.554 was diluted with 12.1 grams of water. CsOH (50% solution in water) in an amount of 0.0352 grams was added to 36 grams of the above silver solution and the resulting mixture was used for the carrier impregnation.

Part C: Catalyst impregnation and curing
Catalyst A:

Approximately 30 g of carrier A (described above in Table 1) is placed under 25 mm vacuum for 3 minutes at room temperature. Approximately 50 to 60 g of doped impregnating solution (as described in Part B above under "For Catalyst A") is then introduced to submerge the carrier, and the vacuum is maintained at 25 mm for an additional 3 minutes. At the end of this time, the vacuum is released, and excess impregnating solution is removed from the carrier by centrifugation for 2 minutes at 500 rpm. If the impregnating solution is prepared without monoethanolamine, then the impregnated carrier is then cured by being continuously shaken in a 300 cu. ft/hr. air stream flowing across a cross-sectional area of approximately 3–5 square inches at 240–270° C. for 3–6 minutes. If significant monoethanolamine is present in the impregnating solution, then the impregnated carrier is cured by being continuously shaken in a 300 cu. ft./hr. air stream at 250° C. to 270° C. for 4–8 minutes. The cured catalyst is then ready for testing. The properties of Catalyst A are shown in Table 3 below.

Comparative Catalyst B:

Comparative Catalyst B was prepared in the same manner as Catalyst A, except that Catalyst carrier B was used in place of Catalyst carrier A and the impregnating solution used was that described In Part B above under "For Comparative Catalyst B". The properties of Comparative Catalyst B are shown in Table 3 below.

Catalyst C:

Catalyst C was prepared in the same manner as Catalyst A, except that Catalyst carrier C was used in place of Catalyst carrier A and the impregnating solution used was that described In Part B above under "For Catalyst C". The properties of Catalyst C are shown in Table 3 below.

Comparative Catalyst D:

Comparative Catalyst D was prepared in the same manner as Catalyst A, except that Catalyst carrier D was used in place of Catalyst carrier A and the impregnating solution used was that described In Part B above under "For Comparative Catalyst D". The properties of Comparative Catalyst D are shown in Table 3 below.

TABLE 3

CATALYST PROPERTIES

|  | Catalyst A | Comparative Catalyst B | Catalyst C | Comparative Catalyst D |
|---|---|---|---|---|
| Ag (wt %) | 14.5 | 14.5 | 14.5 | 14.5 |
| Cs (ppm) | 680 | 560 | 300 | 250 |

The actual silver content of the catalyst can be determined by any of a number of standard, published procedures. The actual level of cesium on the catalyst can be determined by employing a stock cesium hydroxide solution, which has been labeled with a radioactive isotope of cesium, in catalyst preparation. The cesium content of the catalyst can then be determined by measuring the radioactivity of the catalyst. Alternatively, the cesium content of the catalyst can be determined by leaching the catalyst with boiling deionized water. In this extraction process cesium, as well as other alkali metals, is measured by extraction from the catalyst by boiling 10 grams of whole catalyst in 20 milliliters of water for 5 minutes, repeating the above two more times, combining the above extractions and determining the amount of alkali metal present by comparison to standard solutions of reference alkali metals using atomic absorption spectroscopy (using Varian Techtron Model 1200 or equivalent). It should be noted that the cesium content of the catalyst as determined by the water leaching technique may be lower than the cesium content of the catalyst as determined by the radiotracer technique.

Part D: Standard Microreactor Catalyst Test Conditions/Procedure 1 to 3 Grams of crushed catalyst (20–30 mesh) are loaded into a ¼ inch diameter stainless steel U-shaped tube. The U tube is immersed in a molten metal bath (heat medium) and the ends are connected to a gas flow system. The weight of the catalyst used and the inlet gas flow rate are adjusted to achieve a gas hourly space velocity of 6800. The outlet gas pressure is 325 psig.

The gas mixture passed thorough the catalyst bed (in once-through operation) during the entire test run (including startup) consists of 25% ethylene, 7% oxygen, 5% carbon dioxide, 61% nitrogen, and 2.5 to 10 ppmv ethyl chloride as a moderator.

The startup procedure involved ramping the temperature up to 180° C. over a thirty minute period and then up to 190° C. and then up to 200° C. in successive thirty minute periods. Thereafter, the temperature was ramped up at the rate of 10° C. per hour for the next two hours, followed by a further thirty minutes to reach the operating temperature of 225° C., and then the temperature was adjusted to provide 1.5% ethylene oxide at the reactor outlet. Catalyst selectivity ($S_{1.5}$) and catalyst activity ($T_{1.5}$) were measured at those conditions.

The moderator level is maintained at 10 ppmv for six and one-half hours and thereafter at 2.5 ppmv. Due to slight differences in feed gas composition, gas flow rates, and the calibration of analytical instruments used to determine the feed and product gas compositions, the measured selectivity and activity of a given catalyst may vary slightly from one test run to the next.

To allow meaningful comparison of the performance of catalysts tested at different times, the Catalysts A and C, and Comparative Catalysts B and D were tested simultaneously with a standard reference catalyst which was $S_{1.5}$=81.7% and $T_{1.5}$=235° C.

Catalysts A and C and Comparative Catalysts B and D prepared above were tested using the above procedure and the results are given in Table 4 below.

TABLE 4

| CATALYST PERFORMANCE | | |
|---|---|---|
| | $S_{1.5}$, % | $T_{1.5}$, ° C. |
| Catalyst A | 83.3 | 227 |
| Comparative Catalyst B | 82.5 | 235 |
| Catalyst C | 82.5 | 232 |
| Comparative Catalyst D | 81.7 | 235 |

As can be seen in Table 4 above, Catalysts A and C, which were prepared using an alumina based carrier in which a fired body was impregnated with a source of titania, have improved initial activities and selectivities over Comparative Catalysts B and D, respectively, which were prepared using an alumina based carrier with no source of titania impregnated thereon.

What is claimed is:

1. A process for the vapor phase production of ethylene oxide from ethylene and oxygen, said process comprising contacting ethylene in the vapor phase with an oxygen-containing gas at ethylene oxide forming conditions at a temperature in the range of from about 180° C. to about 330° C. in the presence of a catalyst, wherein said catalyst is prepared by a process comprising:
    a) forming a mixture comprising at least one alumina component, ceramic bond, and a liquid medium;
    b) shaping the mixture into carrier bodies;
    c) drying and firing the bodies at a temperature of from 1200° C. to about 1500° C. to form porous carrier bodies;
    d) impregnating the porous carrier bodies with a titania generator in a liquid medium;
    e) calcining the impregnated bodies at a temperature sufficient to remove volatiles and generate titania;
    f) drying the carrier; and
    g) depositing a catalytically effective amount of silver and a promoting amount of alkali metal on said carrier.

2. The process of claim 1 wherein, in the carrier, the dried, fired carrier bodies are impregnated using a titania generator selected from the group consisting of a titania sol and a solution of a titanium compound containing ligands which form volatile products.

3. The process of claim 1 wherein, in the carrier, at least about 80 percent by weight of the ceramic components is provided by alpha alumina.

4. The process of claim 1 wherein, in the carrier, the titania generator is added by impregnation in a volume amount equal to the pore volume of the carrier and sufficient to provide from about 0.05 percent by weight to about 10 percent by weight of titania, basis the weight of the finished carrier.

5. The process of claim 1 wherein, in the carrier, the impregnated carrier is calcined a temperature between about 400° C. and about 1400° C.

6. The process of claim 1 wherein, in the carrier, a ceramic bond material comprising silica, alumina and an alkali metal is added to the extrudable mixture in an amount in the range of from about 1 percent by weight to about 3 percent by weight of the alumina components, expressed as alpha alumina, in the mixture.

7. The process of claim 1 wherein the amount of silver ranges from about 1 percent by weight to about 40 percent by weight of the total catalyst and the alkali metal ranges from about 10 parts per million to about 3000 parts per million, expressed as the metal, by weight of the total catalyst.

8. The process of claim 1 wherein said alkali metal promoter is selected from the group consisting of potassium, rubidium, cesium, lithium and mixtures thereof.

9. The process of claim 8 wherein said promoter is cesium.

10. The process of claim 1 wherein said alkali metal promoter comprises cesium plus at least one additional alkali metal.

11. The process of claim 1 wherein the catalyst additionally comprises a promoting amount of rhenium.

12. The process of claim 11 wherein the catalyst additionally comprises a rhenium co-promoter selected from the group consisting of sulfur, molybdenum, tungsten, chromium, phosphorus, boron and mixtures thereof.

13. A process for the vapor phase production of ethylene oxide from ethylene and oxygen, said process comprising contacting ethylene in the vapor phase with an oxygen-containing gas at ethylene oxide forming conditions at a temperature in the range of from about 180° C. to about 330° C. in the presence of a catalyst, wherein said catalyst is prepared by a process comprising:
    a) forming a mixture comprising:
        i) an alpha alumina having a first component with a median particle size of from about 2 to about 4 microns and a second component with a median particle size of about 4 to about 8 microns;
        ii) a seeded, hydrated precursor of alpha alumina in an amount sufficient to provide from about 5 percent by weight to about 60 percent by weight, basis the total weight of alpha alumina, in the catalyst carrier product;

iii) from about 0 to about 40 percent by weight, based on the weight of the alpha alumina, of a burnout material;

iv) from about 1 percent by weight to about 3 percent by weight, based on the weight of alumina in the composition, expressed as alpha alumina, of a ceramic bond material comprising silica alumina and an alkali metal; and v) water in sufficient quantity to shape the mixture;

b) forming the mixture into the desired shape;

c) firing to convert the seeded precursor of alpha alumina to alpha alumina and form a porous carrier product in which alpha alumina particles with a median particle size of from about 3 microns to about 8 microns are dispersed in a matrix of alpha alumina derived from the seeded precursor material;

d) adding to the porous fired carrier a titania generator selected from the group consisting of an aqueous titania sol and a solution of a titanium compound containing ligands that form volatile products in an amount equivalent to an added titania content in the final carrier formulation of from about 0.05 percent to about 5 percent of the weight of the carrier;

e) calcining the impregnated carrier to remove the solvent and generate the titania;

f) drying the carrier; and g) depositing a catalytically effective amount of silver and a promoting amount of alkali metal on said carrier.

14. The process of claim 13 wherein, in the carrier, the precursor of alpha alumina is seeded with a sub-micron sized particles of alpha alumina in an amount that is from about 0.2 percent by weight to about 5 percent by weight, basis the total alumina weight, measured as alpha alumina, in the catalyst carrier.

15. The process of claim 13 wherein, in the carrier, the impregnated carrier is calcined at a temperature of from 400° C. to about 1400° C.

16. The process of claim 13 wherein the amount of silver ranges from about 1 percent by weight to about 40 percent by weight of the total catalyst and the alkali metal ranges from about 10 parts per million to about 3000 parts per million, expressed as the metal, by weight of the total catalyst.

17. The process of claim 13 wherein said alkali metal promoter is selected from the group consisting of potassium, rubidium, cesium, lithium and mixtures thereof.

18. The process of claim 17 wherein said promoter is cesium.

19. The process of claim 13 wherein said alkali metal promoter comprises cesium plus at least one additional alkali metal.

20. The process of claim 13 wherein the catalyst additionally comprises a promoting amount of rhenium.

21. The process of claim 20 wherein the catalyst additionally comprises a rhenium co-promoter selected from the group consisting of sulfur, molybdenum, tungsten, chromium, phosphorus, boron and mixtures thereof.

22. A process for the production of ethylene oxide wherein ethylene is contacted in the vapor phase with an oxygen-containing gas at ethylene oxide forming conditions at a temperature in the range of from about 180° C. to about 330° C. in the presence of a catalyst prepared by depositing a catalytically effective amount of silver and a promoting amount of alkali metal on a carrier prepared by a process comprising:

a) forming a mixture comprising at least one alumina component, ceramic bond, and a liquid medium;

b) shaping the mixture into carrier bodies;

c) drying and firing the bodies at a temperature of from 1200° C. to about 1500° C. to form porous carrier bodies;

d) impregnating the porous carrier bodies with a titania generator in a liquid medium; and then e) calcining the impregnated bodies at a temperature sufficient to remove volatiles and generate titania, and subsequently drying the carrier having said silver and alkali metal supported thereon.

23. A process for the epoxidation of one or more olefins wherein said olefin is contacted in the vapor phase with an oxygen-containing gas at epoxide forming conditions at a temperature in the range of from about 75° C. to about 325° C. in the presence of an organic halide and a catalyst prepared by the process comprising:

a) forming a mixture comprising at least one alumina component, ceramic bond, and a liquid medium;

b) shaping the mixture into carrier bodies;

c) drying and firing the bodies at a temperature of from 1200° C. to about 1500° C. to form porous carrier bodies;

d) impregnating the porous carrier bodies with titania generator in a liquid medium;

e) calcining the impregnated bodies at a temperature sufficient to remove volatiles and generate titania;

f) depositing a catalytically effective amount of silver and a promoting amount of alkali metal on said carrier, and g) drying the carrier having said silver and alkali metal supported thereon.

* * * * *